(12) United States Patent
Walker

(10) Patent No.: US 6,652,495 B1
(45) Date of Patent: *Nov. 25, 2003

(54) SYSTEM FOR DISPOSAL OF FLUIDS

(76) Inventor: Kenneth Gordon Walker, Suite 24 571 Wardlaw Avenue, Winnipeg, Manitoba (CA), R3L 0M3

( * ) Notice: Subject to any disclaimer, the term of this patent is extended or adjusted under 35 U.S.C. 154(b) by 0 days.

This patent is subject to a terminal disclaimer.

(21) Appl. No.: 09/609,868

(22) Filed: Jul. 3, 2000

Related U.S. Application Data

(63) Continuation of application No. 09/062,551, filed on Apr. 20, 1998, now abandoned, which is a continuation-in-part of application No. 08/627,011, filed on Apr. 3, 1996, now Pat. No. 5,741,237.

(30) Foreign Application Priority Data

Apr. 10, 1995 (CA) ............................................. 2146673
Apr. 19, 1995 (CA) ............................................. 2147292

(51) Int. Cl.[7] ................................................ A61M 1/00
(52) U.S. Cl. ........................ 604/319; 604/317; 604/320; 604/321; 604/322; 604/323; 604/324; 604/326
(58) Field of Search ................................. 604/319–326, 604/317; 215/309; 588/258

(56) References Cited

U.S. PATENT DOCUMENTS

| | | | |
|---|---|---|---|
| 2,848,996 A | 8/1958 | Kowal | |
| 2,896,643 A | 7/1959 | Ottoson | |
| 3,382,886 A | * 5/1968 | Hesselmann | ................ 137/240 |
| 3,612,089 A | * 10/1971 | Beguiristain | ................ 137/205 |
| 3,678,955 A | 7/1972 | Nelson | |
| 3,833,417 A | 9/1974 | Griparis | |
| 3,916,924 A | 11/1975 | McGowan | |
| 4,039,351 A | 8/1977 | Butler | |
| 4,092,993 A | 6/1978 | Stevenson | |
| 4,106,155 A | 8/1978 | Fosslien | |
| 4,111,716 A | 9/1978 | Stevenson | |
| 4,119,114 A | 10/1978 | Bolton et al. | |
| 4,142,545 A | 3/1979 | Billigmeier | |
| 4,144,901 A | 3/1979 | Stevenson | |
| 4,344,469 A | 8/1982 | Brown | |
| 4,384,580 A | 5/1983 | Leviton | |
| 4,386,637 A | 6/1983 | Buchanan | |
| 4,403,611 A | 9/1983 | Babbitt et al. | |
| 4,452,268 A | 6/1984 | Icking et al. | |
| 4,515,283 A | * 5/1985 | Suzuki | ........................ 215/270 |
| 4,673,006 A | 6/1987 | Speck | |
| 4,700,861 A | * 10/1987 | Neward | ...................... 215/309 |
| 4,863,446 A | 9/1989 | Parker | |
| 4,957,491 A | 9/1990 | Parker | |
| 5,117,857 A | 6/1992 | Smith | |
| 5,185,007 A | 2/1993 | Middaugh et al. | |
| 5,242,434 A | 9/1993 | Terry | |
| 5,269,924 A | * 12/1993 | Rochat | ........................ 210/445 |
| 5,380,308 A | 1/1995 | Gunya et al. | |
| 5,449,009 A | 9/1995 | Kerwin et al. | |
| 5,620,428 A | 4/1997 | Hand | |
| 5,634,893 A | * 6/1997 | Riston | ............................ 604/4 |
| 5,713,879 A | * 2/1998 | Schneider | .................... 604/319 |
| 7,797,742 | * 8/1998 | Fraker | ........................... 433/92 |
| 5,807,359 A | 9/1998 | Bemis et al. | |
| 5,914,047 A | 6/1999 | Griffiths | |

* cited by examiner

*Primary Examiner*—Weilun Lo
*Assistant Examiner*—Michael Bogart
(74) *Attorney, Agent, or Firm*—Oyen Wiggs Green & Mutala

(57) ABSTRACT

A system for disposing of body fluids collected during surgery comprises a canister and an apparatus for emptying and cleaning the canister. The canister has a lid having an inlet port to receive body fluids during surgery and for insertion of a cleaning fluid sprayer during servicing, an outlet port with a suction tube extending into the canister for removal of fluids therefrom, and a vacuum port for the application of vacuum to the canister. The servicing unit is an appliance having a receiving compartment in which the canister is placed. A connector head in the servicing unit connects the canister to a source of cleaning fluid and to a conduit for evacuating the fluids in the canister through the suction tube and to a decontamination chamber, where they are brought into contact with a disinfecting fluid, and subsequently to a drain.

17 Claims, 10 Drawing Sheets

SYSTEM FOR DISPOSAL OF FLUIDS

REFERENCES TO RELATED APPLICATION

This application is a continuation of application Ser. No. 09/062,551 abandoned filed Apr. 20, 1998 now abandoned, which is a continuation-in-part of application Ser. No. 08/627,011 filed Apr. 3, 1996, which issued as U.S. Pat. No. 5,741,237 on Apr. 21, 1998.

TECHNICAL FIELD

The invention pertains to a system for disposing of fluids and in particular a system for the safe disposal of body fluids collected during surgical procedures.

BACKGROUND

During surgery and other medical procedures, blood and other potentially infectious fluids are collected which must eventually be disposed of, without undue risk of infection to hospital workers by pathogens that may be present in the fluids. Disposable suction canisters, or disposable liners for canisters, are commonly used at present to collect fluids. These are either incinerated together with the collected fluids, or the fluids may be emptied to a drain by hospital workers and the empty canisters subsequently incinerated or removed to a remote location for disposal. Prior to incineration or disposal, disinfecting or gelling agents are often dispensed in the canisters. The additional handling of canisters required to carry out these procedures increases the likelihood of exposure to the collected body fluids and therefore increases the risk to workers of infection by pathogens in the fluids.

Reusable gravity fed fluid collection devices such as "kickbuckets" are also used in operating rooms, but such devices must typically be emptied and cleaned by hand, or disposable liners in such devices must be disposed of, again exposing workers to the risk of contact with the body fluids during handling. In the present application, all such devices are referred to as canisters.

Sophisticated fluid disposal systems have been described that use specialized collection containers that are used for reuse, such as the device disclosed in U.S. Pat. No. 5,449,009 issued to Kerwin et al. on Sep. 12, 1995. Such units have the disadvantage that they are not adapted for use with standard canisters or with the operating room and hospital fixtures that are commonly adapted to fit standard canisters. The Kerwin et al. device also suffers from an important operational disadvantage. Hazardous fluids are removed from the collection container in Kerwin at al. by introduction of pressurized air into the collection container to displace the hazardous fluids. It will be appreciated that this approach entails some risk of rupturing the collection container and dispersing the hazardous fluids contained in it.

There is a need in the art to provide a system for disposing of body fluids which includes a reusable collection device and which permits disposal of the fluids and cleaning of the collection device for re-use without undue risk of exposure of hospital workers to pathogens in the fluids.

SUMMARY OF INVENTION

In accordance with a preferred embodiment of the invention, there is provided a system for collecting and disposing of body fluids collected during surgery comprising a canister and a servicing unit for removing the body fluids from the canister and cleaning the canister for re-use. The canister is a vessel having sidewalls, a bottom and a lid. The lid has an inlet port for the inflow of body fluids into the canister during surgery and also for the inflow of cleaning fluid during the cleaning of the canister. It has a vacuum port for application of vacuum to the canister to induce the inflow of body fluids into the canister. The lid also has an outlet port with a suction tube extending into the canister for the outflow of body fluids and cleaning fluid from the canister. Means are provided for closing the outlet port when the canister is being used to collect fluids during surgery.

The servicing unit has a body with a compartment which contains the canister while it is being emptied and cleaned. The servicing unit has an outlet conduit to conduct fluid from the canister and an inlet conduit to conduct cleaning fluid from a source of cleaning fluid to the inlet port of the canister. Means are provided to control the flow of fluids through the fluid conduit means. The servicing unit includes a decontamination chamber into which body fluid from the canister is emptied and in which the body fluid comes in contact with disinfectant before being released to a drain.

The compartment in the servicing unit into which the canister is placed has a lift mechanism for raising and lowering it, to raise the canister for connection to the inlet and outlet conduits of the servicing unit.

In another preferred embodiment of the canister, the lid has four ports, rather than three, separate ports being provided for the inflow of body fluid during surgery and for the inflow of cleaning fluid during cleaning of the canister, rather than a single port serving both functions.

BRIEF DESCRIPTION OF DRAWINGS

In drawings which illustrate embodiments of the invention.

DETAILED DESCRIPTION OF THE INVENTION

A system for disposal of body fluids collected during surgery comprises a canister which acts as a collection device and a servicing unit for emptying the fluids from the canister and cleaning the canister for re-use.

Figure 1:
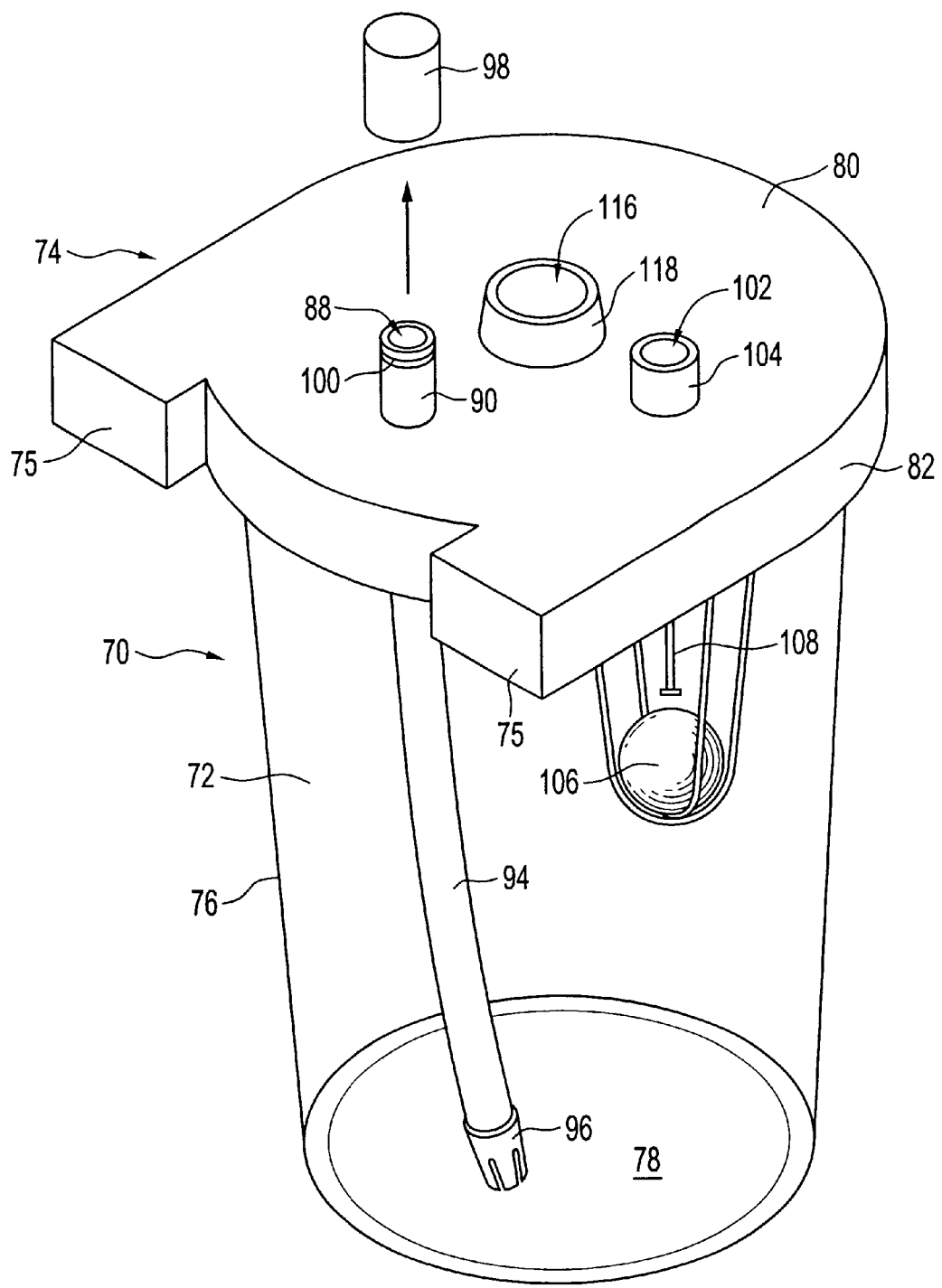
FIG. 1 is a perspective view of one embodiment of the canister.
Figure 2:
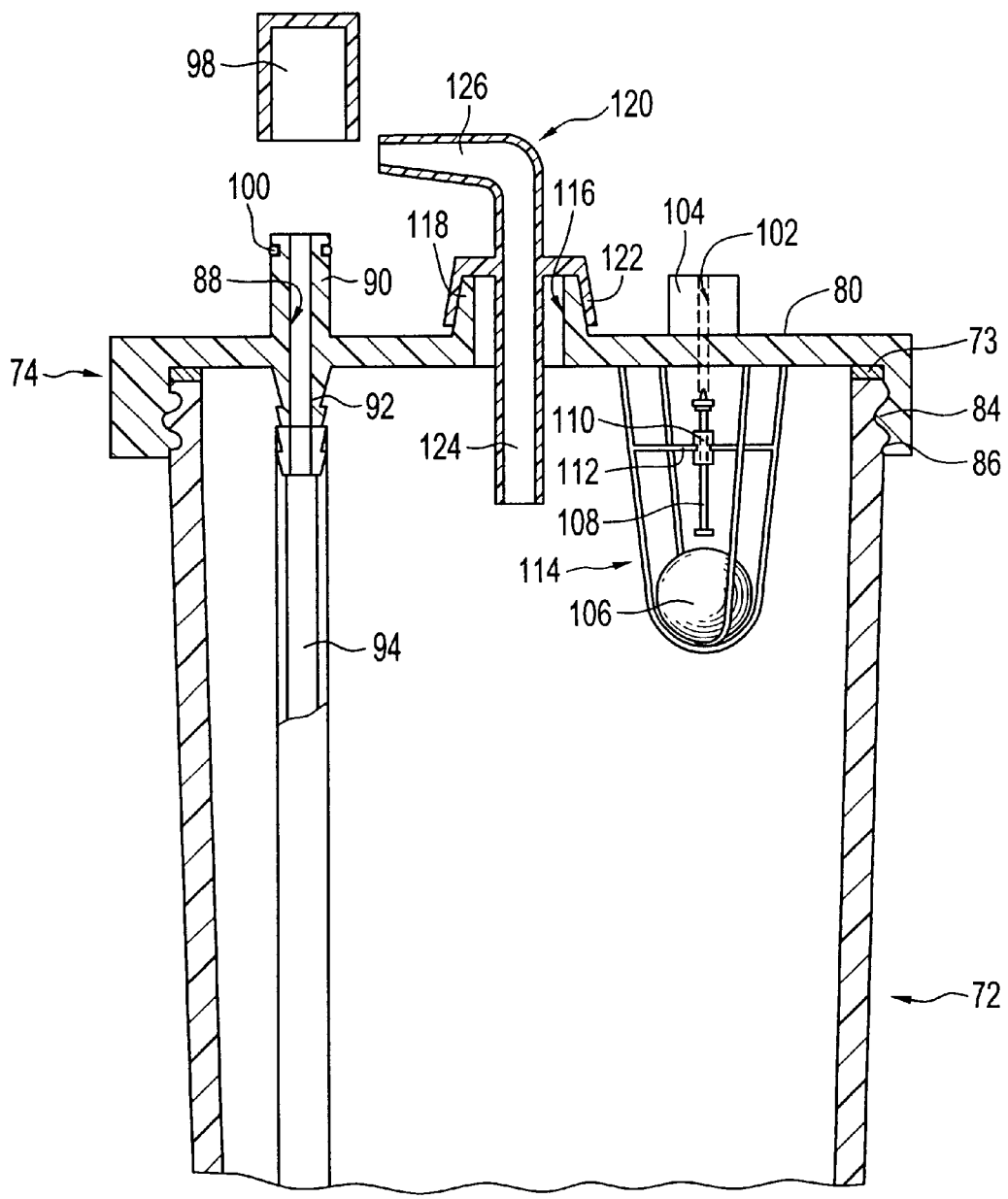
FIG. 2 is a vertical cross-section view of the canister of FIG. 1.

Referring to FIGS. 1 and 2, which illustrate a first embodiment of the canister, the canister 70 has a body 72 and lid 74. Body 72 has sidewalls 76 and a substantially flat bottom 78. Lid 74 has a generally flat top 80 and circumferential rim 82 with threads 84 which engage mating threads 86 on the upper lip of the body 72 to affix and seal lid 74 to body 72. A gasket 73 is provided to assist in sealing engagement of lid 74 to body 72. Lid 74 has two protrusions 75 along one edge thereof.

Lid 74 has three openings therein which extend into canister 70.

Outlet port 88 extends through outlet nipple 90 and suction tube fitting 92. Suction tube 94 is connected to the suction tube fitting 92 and extends to the bottom of the canister and terminates in a strainer 96 adjacent bottom wall 78. Port 88 is used in the suctioning of fluid from the canister, as described below. Nipple 90 is fitted with removable cap 98, which fits over nipple 90 and engages O-ring 100, sealing port 88 when port 88 is not in use.

Port 88 preferably has a puncturable membrane (not shown) at the top of nipple 90, of the type shown in U.S. Pat. No. 5,033,777 Blenkush, FIG. 4. In such case the connector head of the servicing unit includes a needlelike end on the connector fitting for puncturing the membrane.

Vacuum port 102 is fitted with a nipple 104 extending vertically upward therefrom and adapted to connect to a vacuum conduit. A check valve to prevent overflow of body fluid from vacuum port 102 is provided, comprising floatball 106 and needle valve 108. Needle valve 108 is slidably retained in guide sleeve 110 supported by radial arms 112 of floatball cage 114. The floatball is selected to be of a size and buoyancy sufficient to readily raise the needle valve to close the vacuum port when the floatball is floated on the surface of fluid in the canister. A variety of vacuum port check valve designs are possible, preferable designs have a minimal surface area and profile to lessen interference with the cleaning process. During the collection of body fluids, when the fluid level in the canister 70 becomes sufficiently high, floatball 106 is floated upward and abuts against needle valve 108, stopping the application of vacuum to canister 70.

Inlet port 116 extends through lid 74 and serves the dual function of inlet for body fluid during surgery and inlet for cleaning fluid during cleaning of the canister 70. Inlet port 116 is fitted with nipple 118 extending vertically upward therefrom. Removable inlet tube 120 is fitted to the canister 70 for use in collecting body fluid. Inlet tube 120 is an angled or straight tubular member having a flange 122 adapted to sealingly engage nipple 118 and hold inlet tube 120 thereon. Inlet tube 120 has a straight portion 124 which extends through port 116 and into the body of the canister, and angled portion 126 which extends at a right angle to portion 124. Portion 126 tapers inwardly toward its free end and is adapted to connect to a body fluid conduit.

For cleaning of the canister 70, inlet tube 120 is removed from nipple 118 and inlet port 116 is used for the inflow of cleaning fluid, as described below.

When canister 70 is being used for collecting body fluids during surgery, cap 98 is put in place to seal nipple 90, a vacuum conduit is connected to nipple 104 and a body fluid inflow conduit is connected to inlet tube 120. Vacuum is applied through the vacuum conduit, inducing the flow of body fluids into the canister, in which they are collected. When the canister is full, it can be disconnected from the vacuum conduit and body fluid inflow conduit. The canister is then ready to be emptied and cleaned in the servicing unit.

Figure 3:
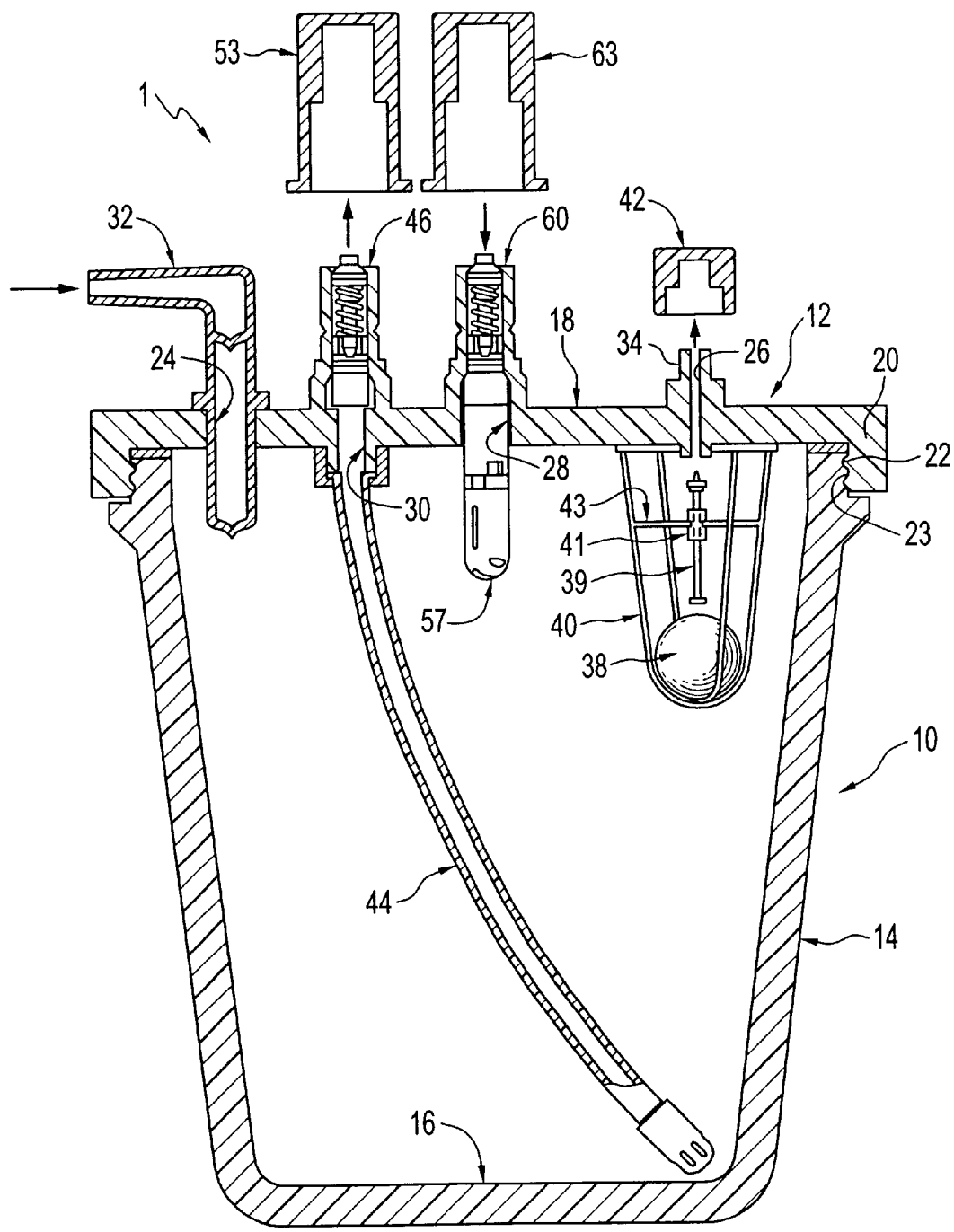
FIG. 3 is a vertical cross-section view of a second embodiment of the canister.

Referring next to FIG. 3, which illustrates a second embodiment of the canister, having four ports rather than three, the canister 1 has a body 10 and lid 12. Body 10 has sidewalls 14 and a substantially flat bottom 16. Lid 12 has a generally flat top 18 and circumferential rim 20 with threads 22 which engage mating threads 23 on the upper lip of the body 10 to affix and seal lid 12 to body 10, a gasket is provided to assist in sealing engagement of lid 12 to body 10. Lid 12 has two protrusions (not visible in FIG. 3) the same as protrusions 75 of the embodiment of FIG. 1, for engagement in the servicing unit.

Lid 12 has four openings therein which extend into canister 1, two of which are used for the collection of body fluids during surgery, namely fluid inlet port 24 and vacuum port 26; and two of which are used for emptying and cleaning of the canister, namely inlet port 28 and outlet port 30. It will be appreciated that ports 24, 26, 28, 30 in lid 12 may be positioned in a wide variety of ways relative to one another. Similarly, lid 12 may be provided with other ports for use in a variety of applications.

Inlet port 24 has inlet tube 32 fitted therein, adapted to connect to a conduit to conduct body fluids to the canister during surgery. Inlet tube 32 is provided with one-way valves to inhibit reverse flow of body fluids. Inlet tube 32 may be removably attached to inlet port 24 and may be disposable. Vacuum port 26 is fitted with a nipple 34 extending vertically outward therefrom and adapted to connect to a vacuum conduit. A check valve to prevent overflow of body fluid from vacuum port 26 is provided, consisting of floatball 38 and needle valve 39. Needle valve 39 is slidably retained in guide sleeve 41 supported by radial arms 43 of floatball cage 40. During the collection of body fluids, when the fluid level in the canister 1 becomes sufficiently high, floatball 38 is floated upward against needle valve 39, stopping the application of vacuum to canister 1. Cap 42 fits over nipple 34 to seal vacuum port 26 when the vacuum conduit is removed from nipple 34, to seal the vacuum port 26 and prevent spillage of fluid through it.

Outlet port 30 extends through lid 12. Suction tube 44 is fitted to the inner end of port 30, extending into canister 1 and terminating in a strainer end adjacent bottom wall 16. Suction tube 44 and the strainer end may be disposable. Nipple 46 extends outwardly from port 30 and is adapted to be connected to the servicing unit, as described below. Nipple 46 may be fitted with a check valve, in the form of a standard hydraulic quick-connector. Cap 53 is used to seal nipple 46 when port 30 is not in use.

Nipple 60 is connected through port 28 in lid 12 to rotatable sprayhead 57. Sprayhead 57 has orifices disposed thereon and is adapted to spray cleaning fluid flowing into canister 1 against the interior parts of the canister. Sprayhead 57 may be a rotatable nozzle similar in design to compact keg washing nozzles available from Spraying Systems Co. of Wheaton Ill., with orifices disposed to actuate rotation of sprayhead 57 and provide an appropriate dispersal of fluid in canister 1. Nipple 60 may be fitted with a check valve, as in a standard hydraulic quick-connector, and is adapted to connect to the servicing unit, as described below. Cap 63 may be used to seal nipple 60 when it is not in use.

When canister 1 is being used for collecting body fluids during surgery, caps 63 and 53 are put in place to seal nipples 60 and 46, a vacuum conduit is connected to nipple 34 and a body fluid inflow conduit is connected to inlet tube 32. Vacuum is applied through the vacuum conduit, inducing the flow of body fluids into the canister, in which they are collected. When the canister is full, it can be disconnected from the vacuum conduit and body fluid inflow conduit and cap 42 placed over nipple 34. The canister is then ready to be emptied and cleaned in servicing unit, as described below.

Figure 10:
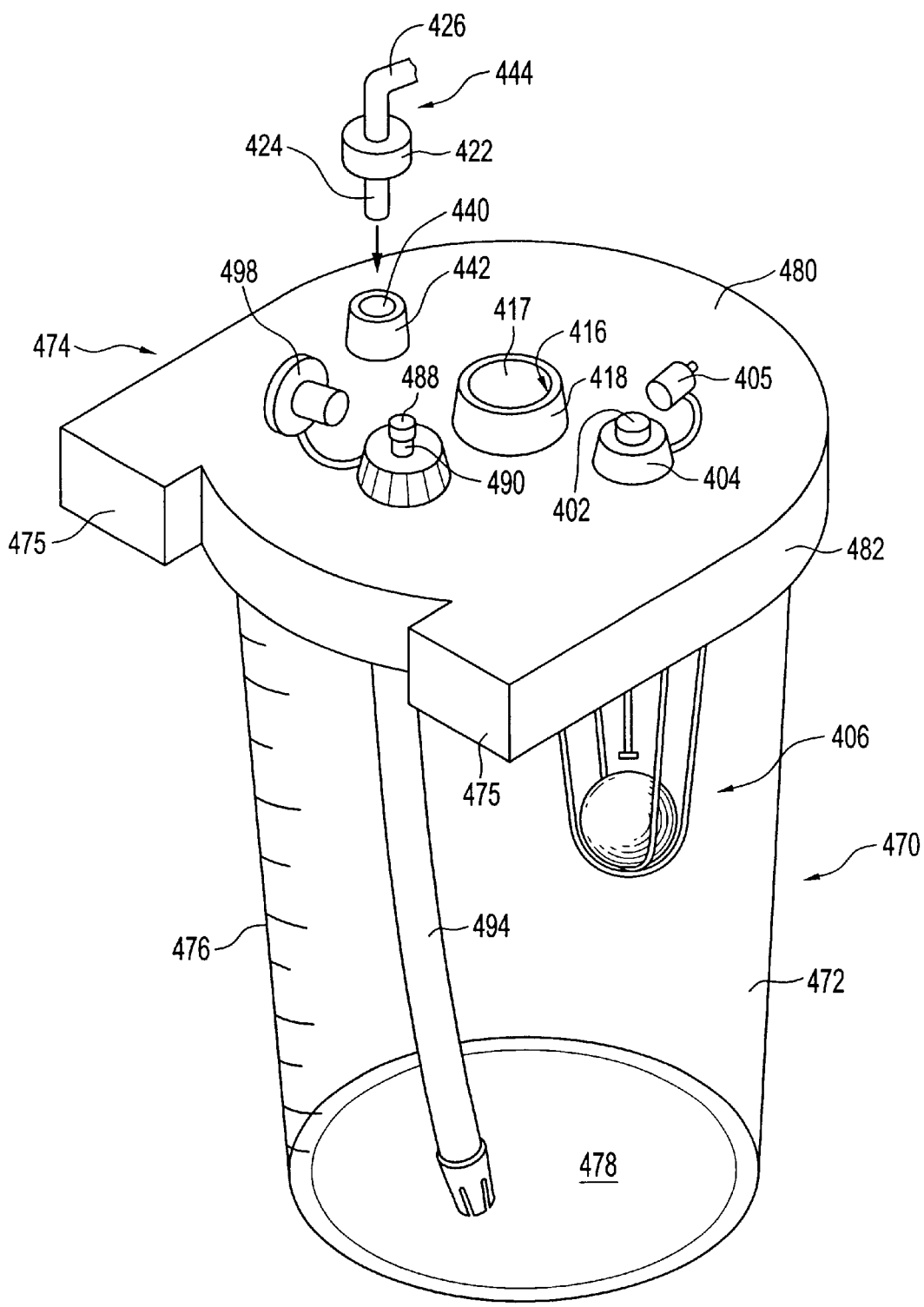
FIG. 10 is a perspective view of a third embodiment of the canister.

FIG. 10 illustrates a third embodiment of the canister, which is similar to the embodiment of FIG. 1 but has two inlet ports in the lid. Canister 470 has a body 472 and lid 474. Body 472 has side walls 476 and a substantially flat bottom 478. Lid 474 has a generally flat top 480 and a circumferential rim 482 with threads which engage mating threads on the upper lip of the body to affix and seal the lid to the body. Lid 474 has two protrusions 475 along one edge thereof. Lid 474 has four openings therein which extend into canister 470. Outlet port 488 extends through outlet nipple 490 and connects to suction tube 494. Port 488 is used in the suctioning of fluid from the canister. Nipple 490 is fitted with removable and tethered cap 498 which seals port 490 when it is not in use.

Vacuum port 402 is fitted with nipple 404 extending vertically upward therefrom and adapted to connect to a vacuum conduit. Nipple 404 is fitted with removable and tethered cap 405. A check valve 406 that is the same as the check valve of FIG. 1 is attached to lid 480, to prevent overflow of body fluid from vacuum port 402.

Inlet port 416 is fitted with nipple 418. The opening across the top of nipple 418 is closed by rupturable membrane 417. Port 418 is intended for the insertion of a sprayer during the cleaning of the canister in the servicing unit, so membrane 417 is adapted to be ruptured by insertion of the sprayer.

Inlet port 440 extends through lid 480 into canister 470 and is fitted with nipple 442. Removable inlet tube 444 has flange 422 adapted to sealingly engage nipple 442 and hold inlet tube 444 thereon. Inlet tube 444 has a straight portion 424 which extends through port 440 and into the body of the canister, and angle portion 426 which extends at an angle to portion 424. Portion 426 tapers inwardly toward its free end and is adapted to connect to a body fluid conduit.

When canister 470 is being used for collecting body fluids during surgery, cap 498 is put in place to seal nipple 490, a vacuum conduit is connected to nipple 404 and a body fluid inflow conduit is connected to inlet tube 444. A cap (not shown) is fitted to nipple 419 to seal inlet port 416. Vacuum is applied through the vacuum conduit, inducing the flow of body fluids into the canister, in which they are collected. When the canister is full, it can be disconnected from the vacuum conduit and body fluid inflow conduit. The canister is then ready to be emptied and cleaned in the servicing unit.

Figure 4:
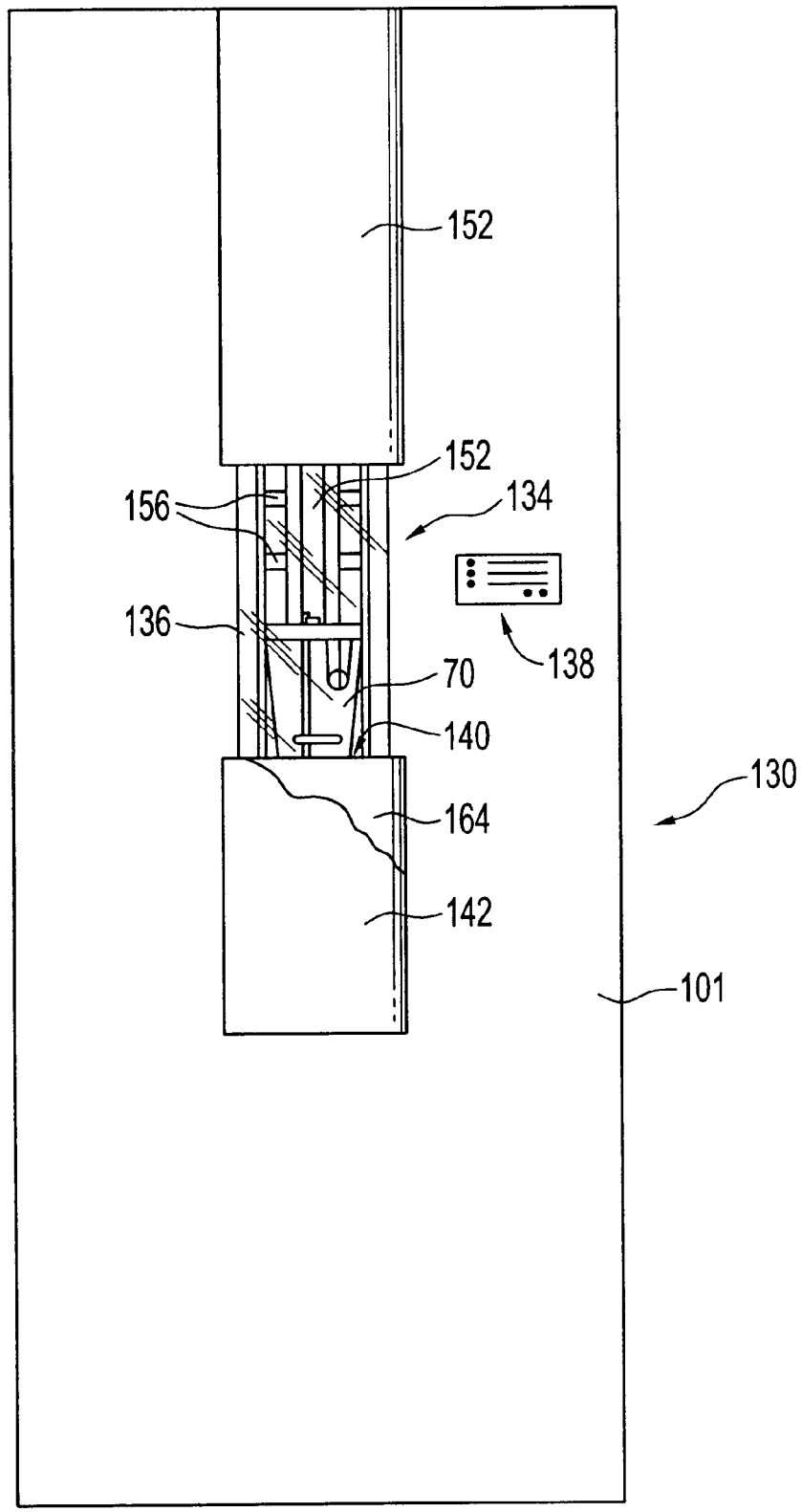
FIG. 4 is a front elevation view of the servicing unit holding a canister.

The servicing unit will next be described in conjunction with servicing the canister of the embodiment of FIG. 1. Referring to FIG. 4, servicing unit 130 is a generally rectangular apparatus having an outer wall 101 and a receiving compartment 134 in which a canister is placed for servicing, i.e. for removal of the collected body fluids and cleaning of the canister.

Canister holding compartment 134 is open at the front of the servicing unit 130 for access. It has a transparent door 136 which slides downwards to cover the opening for worker protection during servicing of canister 70. Control video display panel 138 on the front of the servicing unit contains the controls for operating the unit.

Canister holding compartment 134 has a platform 140 on which canister 70 is placed for servicing. Extending below the platform 140 of the canister holding compartment 134 is a semi-cylindrical outwardly curving wall section 142 extending from the front face of the servicing unit 130. Similarly, above the canister holding compartment 134 is an upper, semi-cylindrical outwardly curving wall portion 144 extending from the front face of the servicing unit.

Figure 5:
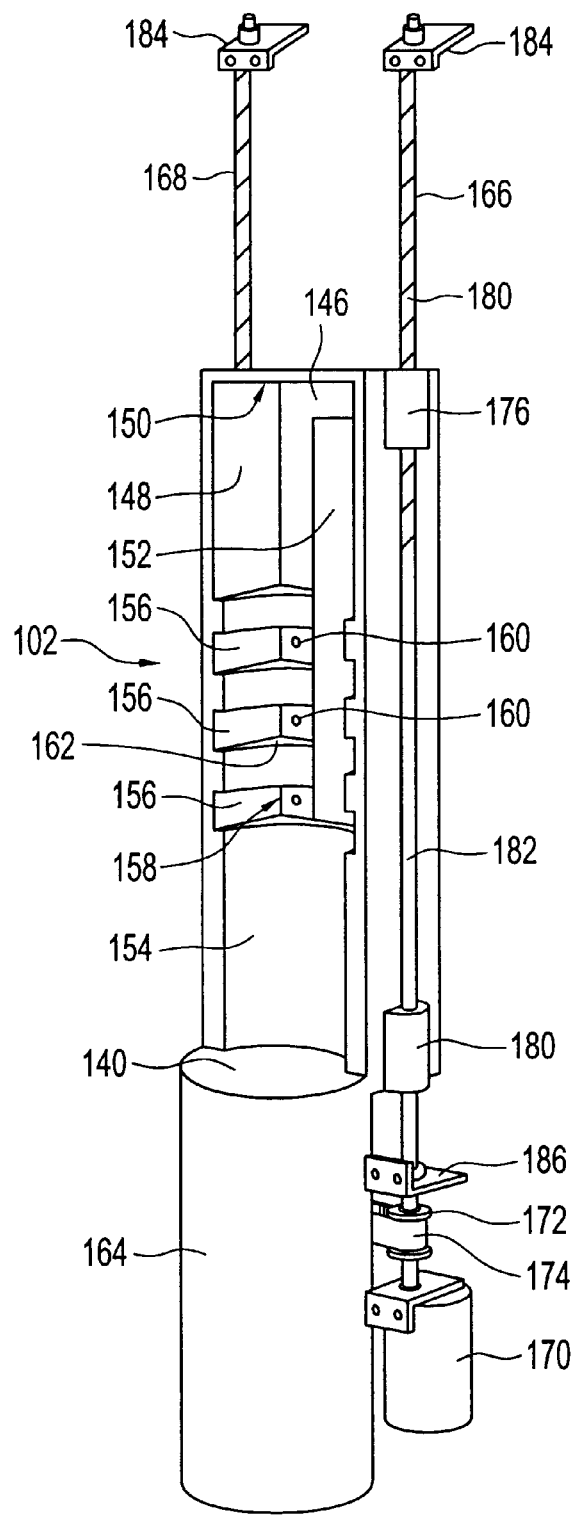
FIG. 5 is a perspective view of the canister holding compartment and lift mechanism of the servicing unit.

Referring to FIG. 5, the canister holding compartment 134 has an open front, a rear wall 146, side walls 148, platform 140 and upper wall 150. The rear wall 146 has an elongated opening 152 defining a passage into the compartment 134. The interior of the compartment has an inwardly curving surface 154 to accommodate the cylindrical shape of a canister. In the upper half of the compartment 134, the curved surface 154 is broken at intervals by pairs of horizontal recessed slots 156. These recessed slots receive the protruding corners 75 of a canister lid, and are located at elevations corresponding to the height of a canister when a canister is resting upon the platform 140. The inside corner 158 of a recessed slot 156 meets with the ninety degree angle of protruding corner 75 on a canister lid, so that when canister 70 is inserted into the compartment, the canister is retained in a position for a connection to the connector head 188 (shown in FIG. 6) of the servicing unit 130. Location indicators 160 in the form of pin or lever switches are fixed within the recessed slots 156 so that when the protrusions 75 on a canister lid are pushed into a pair of recessed slots 156, the protrusions will come into contact with the location indicators 160, which will in turn send a signal to a controller indicating that the canister is fully inserted within the compartment 134. The shape of the canister lid, the recessed slots in the compartment and the location indicators within the recessed slots ensure that there is only one orientation in which a canister can be correctly placed within the compartment. The recessed slots also provide an overhanging ledge 162 above each slot that restrains the canister from upward movement during disconnection from the connector head when the canister compartment is lowered. Ball detents (not shown) may also be provided within the recessed slots 156 to meet with corresponding dimples on the sides or undersurfaces of the canister lid protrusions 75 so that the canister will click into position when inserted. A plurality of recessed slots 156 at various heights allow several capacities of canisters to be accommodated by the compartment 134. FIG. 5 illustrates three pairs of slots 156 at different heights for receiving canisters of 1000 cc, 1500 cc and 3000 cc capacities.

The elongated opening 152 in the rear wall 146 of the canister holding compartment 134 provides a passageway through which conduits which connect to the connector head 188 may pass from the interior of the servicing unit 130 into the compartment 134 and to the connector head where they are mounted. The opening 152 extends vertically a sufficient length for the compartment 134 to travel the distance required to raise the smallest size canister up to the connector head and lower it again to the rest position.

Extending below the platform 144 of the canister holding compartment 134 is a semi-cylindrical skirt 164. When the compartment 134 is raised, the skirt 164 covers the opening into the servicing unit housing under the platform 140. When the compartment 134 is lowered to its rest position, the skirt 164 slides behind outwardly curving wall section 142 on the front of the servicing unit.

The vertical lift mechanism for the canister compartment 134 comprises two parallel lead screw shafts 166, 168 which support the compartment in an upright position and move it vertically. A motor 170 provides rotational force on lead screw shaft 166. The second lead screw shaft 168 is coupled to the first by means of pulley 172 and cogged timing belt 174. Rotation of the first lead screw accordingly drives the second lead screw synchronously. A pair of threaded blocks 176 are attached to the exterior sidewalls of the compartment at its upper end and a pair of guide blocks 180 with bushings at its lower end, adjacent the platform 140. Each lead screw shaft 166, 168 has a threaded upper section 180 and a smooth lower section 182. The upper section 180 is threaded through the threaded block 176 and the smooth lower section 182 passes through the guide block 180. Rotation of the lead screw shafts 166, 168 causes the threaded blocks 176 to ride up the threaded sections 180 of the shafts 166, 168 and move the canister compartment 134 upward. The lower guide blocks 180 glide along the smooth section 182 of the lead screws 166, 168 when the canister compartment is in motion. The lower sections 182 of the lead screws 166, 168 may also be threaded if desired, and the lower blocks 180 may have threaded drive nuts to distribute the weight bearing on the shafts 166, 168 and provide driving force. To support the lead screw shafts 166, 168 each shaft has at its top end a mounting bracket 184 with bearings, which is secured to the top of the servicing unit housing; and a mounting bracket 186 with bearings at its lower end, which is secured to the front wall of the servicing unit housing.

Alternate means for providing vertical lift for the canister holding compartment 134 may be provided and include various electro-mechanical linear actuators such as a motor driven jacking screw, motor driven rack and pinion, scissor jack, linear motor, ball screw and motor, long stroke electromagnetic solenoid, pneumatic cylinder and hydraulic cylinder.

Figure 6:
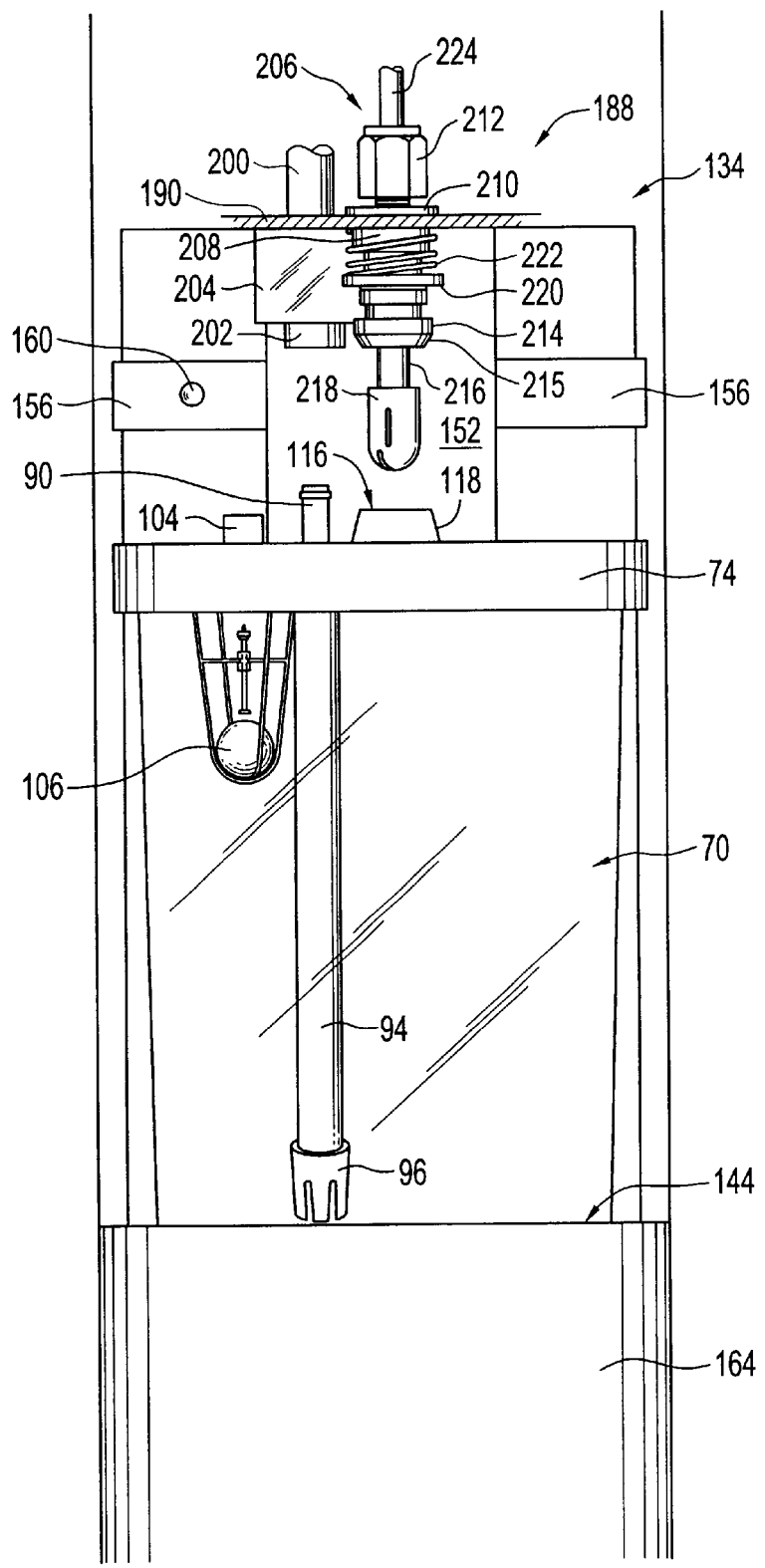
FIG. 6 is a front elevation view of the connector head in the servicing unit.

FIG. 6 illustrates how the connector head, indicated generally at 188, connects a canister to conduits within the canister holding compartment 134. Connector head frame 190 is mounted in the servicing unit by means of a bracket (not shown) extending through elongate opening 152 in the canister holding compartment 134. Coupling 202, which is adapted to fit over nipple 90 of the canister lid 74, is affixed to connector head frame 190 by mounting bracket 204, and is operatively connected to outlet conduit 200. When the canister is raised for connection to the connector head 134, coupling 202 is brought into sealing engagement with nipple 90 so that fluid in the canister may be evacuated through suction tube 94, and into outlet conduit 200. Spray assembly 206 is also affixed to connector head frame 190. The spray assembly 206 has a nozzle housing guide bushing 208 and stop flange 210 held on opposite sides of the connector head frame 190 by means of fitting 212. Seal fitting 214 is adapted for sealing engagement with the upper edge of nipple 118 on the canister lid 74. Nozzle pipe 216 extends through the sprayhead, terminating in spray nozzle 218. Spring seat collar 220 is biased away from connector head frame 190 by compression spring 222. When the canister is raised for connection to the connector head 188, nozzle pipe 216 and spray nozzle 218 extend through port 116, and the bevelled portion of seal fitting 214 seals against the upper edge of nipple 118. Inlet conduit 224 extends through the spray assembly 206 for delivery of cleaning fluid through spray nozzle 218.

Figure 7:
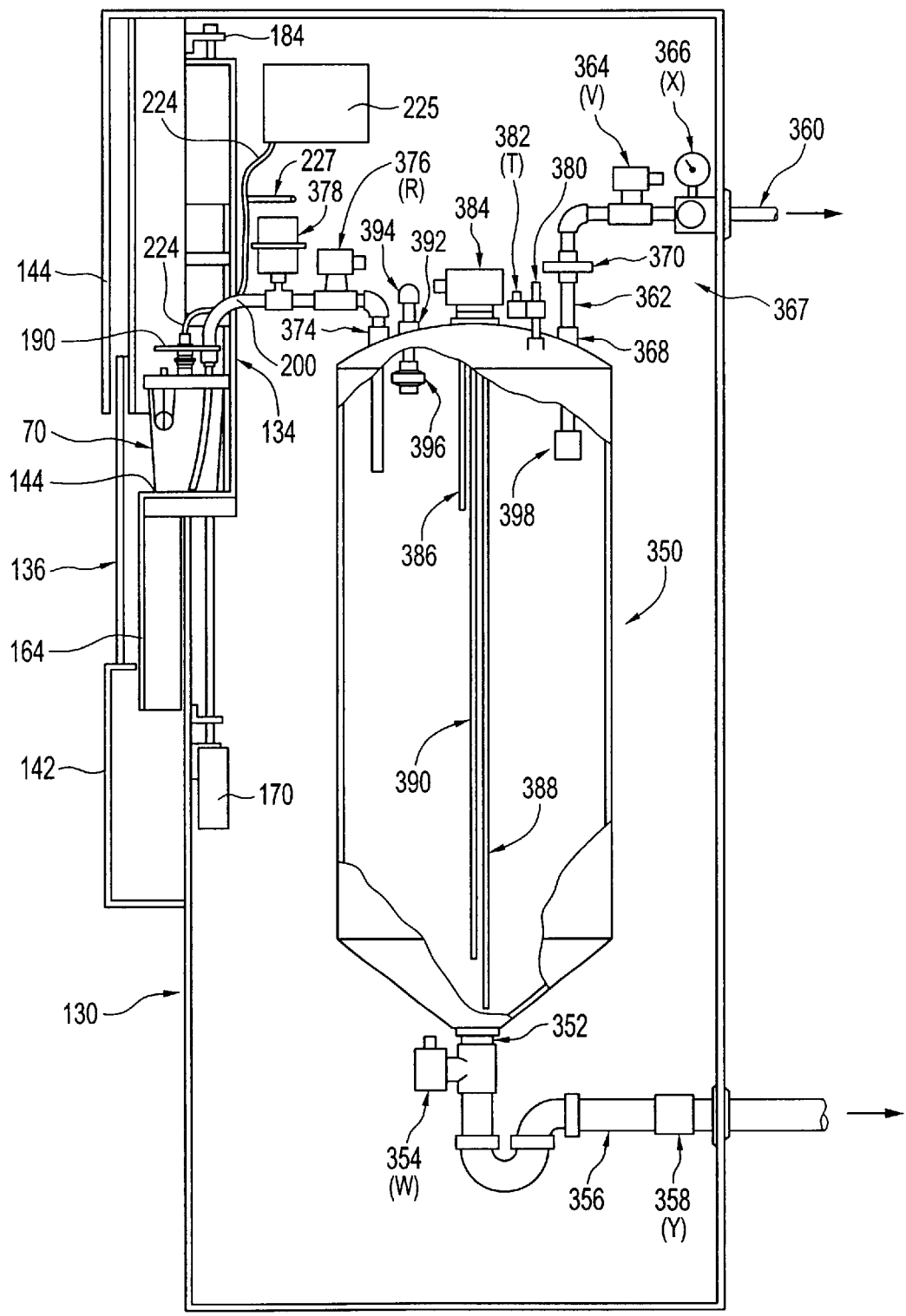
FIG. 7 is an elevation view, partly cutaway, of the servicing unit.
Figure 8:
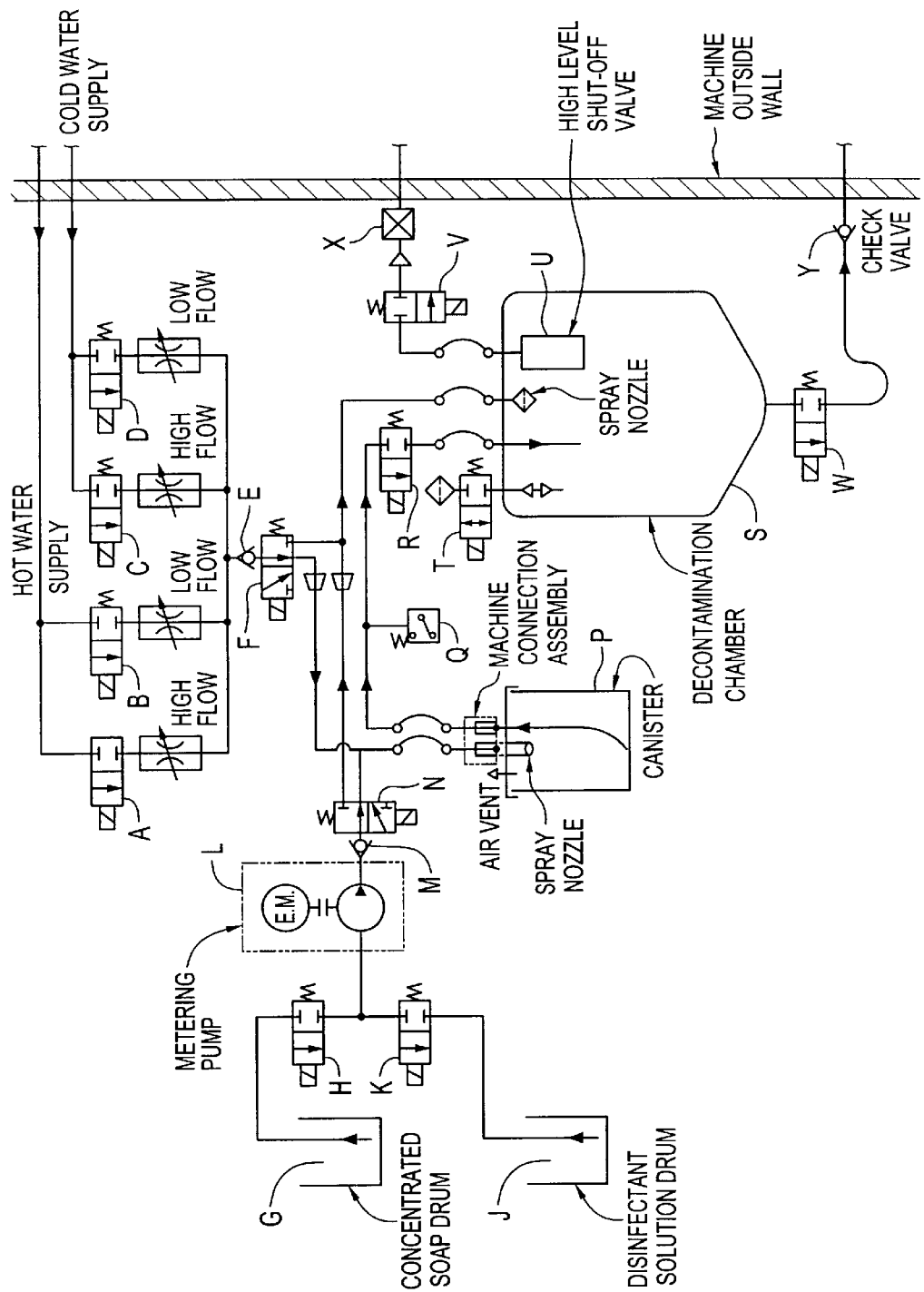
FIG. 8 is a schematic view of the fluid circuit of the servicing unit.

FIG. 7 illustrates the interior of servicing unit 130 and FIG. 8 is a schematic view of fluid circuit of the servicing unit. The servicing unit provides for removal of the body fluids from a canister 70 and the cleaning of the canister for further use.

The servicing unit 130 preferably includes a decontamination chamber 350, which is a receptacle having an inlet which receives body fluids and washing fluids from the canister 70, an air vent for communication with the atmosphere, a second inlet for receiving washing fluid and disinfectant, a vacuum outlet for connection to a vacuum supply, liquid level sensors, a drain, and valves for controlling the functions of the chamber during operation.

The servicing unit 130 includes a reservoir 225 of a detergent for cleaning the canister. It is connected to canister 70 by inlet conduit 224. A supply of water (not shown) connects by conduit 227 to conduit 224 so that detergent and water mix in conduit 224 before delivery to the canister.

The decontamination chamber 350 is a tank-like structure made of steel or fibreglass or other suitable material and having sufficient capacity to receive the contents of several canisters and the corresponding volume of washing fluid consumed with each canister servicing cycle. The chamber has a drain 352 at its lower end which is controlled by a solenoid valve or electro-mechanically actuated ¼-turn ball valve 354. The valve 354 is closed when the decontamination chamber 350 is supplied with vacuum and receiving fluids from a canister 70. A drain conduit 356 is provided for draining the contents of the decontamination chamber and may be provided with a check valve 358 if the conduit 356 is to be connected directly to a sewage disposal system. The drain conduit 356 may also be directed to a passive floor drain, in which case the conduit will require neither a trap nor a check valve.

The decontamination chamber 350 is connected at its upper end to a vacuum supply, a conduit 200 for conducting fluid from the canister to the decontamination chamber, an inlet 392 for rinsing and disinfecting fluid and an air vent 380. A conductance probe-type liquid level control system 384 is also mounted on the upper part of the decontamination chamber. A medical vacuum line 360, connected to the vacuum supply (not shown), is connected to the decontamination chamber for providing vacuum thereto. Vacuum is set with regulator 366 within the servicing unit 130, or it may be regulated externally of the servicing unit. An electro-mechanically actuated ¼ ball valve or solenoid valve 364 is provided to turn on and off the supply of vacuum from the regulator 366 to the decontamination chamber 350. A conduit 362 connects the valve 364 to the vacuum outlet 368 on the decontamination chamber and is provided with a microporous filter 370 to prevent aerosols from entering the vacuum line. If medical vacuum is unavailable in the location in which the servicing unit is to be used, a vacuum pump may be employed to provide vacuum to the decontamination chamber.

Fluids suctioned from the canister 70 enter the inlet 374 of the decontamination chamber via conduit 200, which communicates with the connector head 188 of the servicing unit. A vacuum switch 378 monitors the vacuum in the conduit 200 and controls the initiation of the canister rinsing cycle.

Air vent 380 is connected to the decontamination chamber 350 to provide communication with the atmosphere during the draining of the chamber, and to stop the flow of fluid through the inlet port 374 when the volume of fluids in the decontamination chamber has reached a predetermined maximum level. This is done by allowing air to enter the decontamination chamber 350 through air vent 380 to destroy the vacuum present in the chamber. The air vent 380 is also used as a control valve between canister servicing cycles for controlling the application of vacuum to the conduit 200. The operations of the solenoid valve 376 on the fluid circuit and the air valve 380 are coordinated so that at the end of a canister servicing cycle, when the solenoid 376 on the conduit 200 is closed, the air vent 380 is opened. Thus, if several canisters require servicing consecutively, the vacuum supply to the decontamination chamber 350 need not be shut off between canisters. The decontamination chamber 350 would draw air through the air vent 380 until such time as the next canister is connected for service. Once the canister outlet port 88 is connected to outlet conduit 200, the solenoid valve 376 will first be opened and then the air vent 380 will be closed by air vent valve 382. The closing of the air vent 380 will cause vacuum to be applied to the conduit 200 and to the suction tube 94 in the canister. A time out operation may be programmed into the controller to turn off the vacuum to the decontamination chamber 350 if the servicing unit 130 is inactive for a specified time.

Liquid level sensors are provided to control the operation of the decontamination chamber. A probe-type liquid level sensing device 384 is provided to monitor liquid levels in the decontamination chamber, to initiate the draining and rinsing cycle once fluids in the chamber reach a predetermined level, and to monitor the quantity of disinfectant solution delivered to the decontamination chamber following the draining and rinsing cycle. A variety of suitable and commercially available liquid level sensing and control devices may be used for this purpose, including ultrasonic, capacitive, inductive and float devices.

When the decontamination chamber 350 has received the last of a pre-set number of canister cycles, or when high-level liquid level probe 386 in the decontamination chamber 350 indicates that the decontamination chamber is full, solenoid valve 382 will energize, opening air vent 380 and allow air to enter the interior of the decontamination chamber. Valve 376 on outlet conduit 200 will close. The drain valve 354 will open and allow the contents of the decontamination chamber 350 to drain out of drain conduit 356. The low level liquid sensor probe 388 will sense when the decontamination chamber 350 has drained and send a signal to the controller to begin the rinse cycle.

During the decontamination chamber rinse cycle, the drain valve 354 remains open. Three-way valve F changes position, directing the water flow to the decontamination chamber line 394. Valve A opens and hot water is directed by valve F to the decontamination chamber line 394. 3-way valve N changes position, directing flow to decontamination chamber line 394. Valve H for concentrated detergent opens, metering pump L starts and draws detergent from reservoir G. Detergent is directed by 3-way valve N to the decontamination chamber line 394. The detergent mixes with the hot water flowing through the decontamination chamber line 394, and the mixture of hot water and detergent is delivered through the decontamination chamber inlet 392 to spray nozzle 396 and dispersed against the interior walls of the decontamination chamber 350. The rinsing fluid drains out of drain 356, which remains open during the rinsing cycle. The hot water and detergent rinse is followed by a warm water rinse. Valve H closes, and metering pump L stops. Valve A remains open, and valve D opens. Warm water flows through the decontamination chamber line 394, through the decontamination chamber inlet 392 to the spray nozzle 396 in decontamination chamber 350 and dispersed in the interior of the decontamination chamber 350. When the rinse cycle is complete, valves A and D close.

Following the rinse cycle, the drain valve 354 will close, and a quantity of disinfectant solution will be delivered to the decontamination chamber 350 and retained within the decontamination chamber 350. Cold valve C is opened, disinfectant valve K is opened, and metering pump L starts. Disinfectant is drawn from reservoir J. The disinfectant is directed by 3-way valve N to the decontamination chamber line 394. The disinfectant mixes with the cold water flowing through the decontamination chamber line 394 and is delivered through the decontamination chamber inlet 392 to spray nozzle 396. The disinfectant level probe 390 indicates when a sufficient quantity of disinfectant solution has accumulated in the decontamination chamber 350. When the liquid level of the disinfectant solution rises sufficiently to come in contact with probe 390, a signal is sent to the controller. Metering pump L stops, disinfectant valve K is closed and cold water valve C is closed. Three-way valve N returns to normal position (directed to canister line) and 3-way valve F returns to normal position (directed to canister line). The decontamination chamber 350 is again ready to receive fluids from canister servicing cycles.

Figure 9:
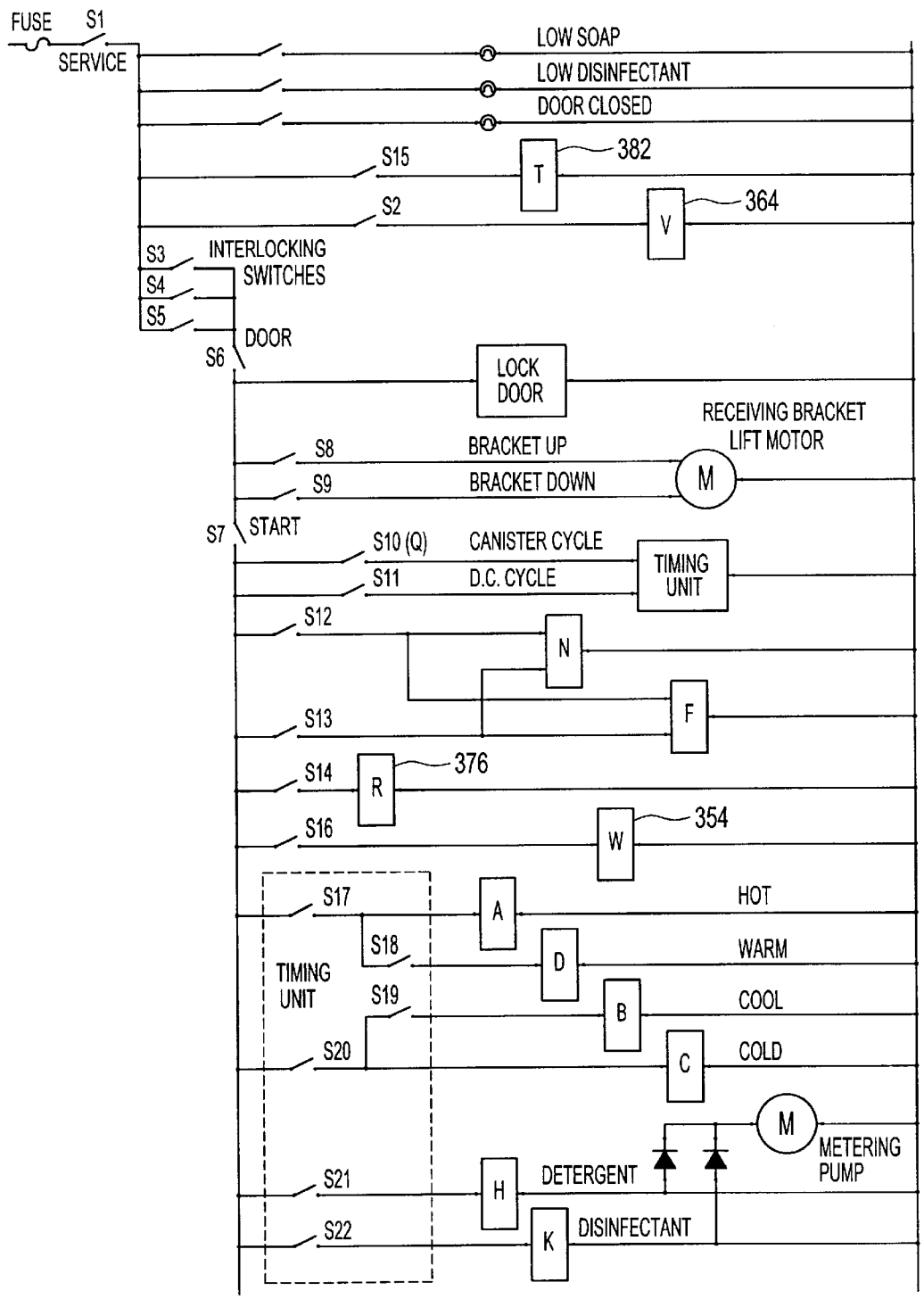
FIG. 9 is a schematic view of the electrical control system of the servicing unit.

As shown in electrical schematic FIG. 9, controls are provided for the various functions of the servicing unit. Conventional electrical controls, such as programable electronic controls, of types well known to persons skilled in the art, are provided to control (a) the actuation and speed of pumps; (b) the actuation, speed and direction of motors; (c) the opening and closing of valves; and (d) indicators to provide information to operators on control video display panel 138. Liquid level sensors for each of the reservoirs may be used to send signals to the control video display panel if fluid levels are low and require replenishment. Switches may also be provided that ensure that the transparent door 136 is closed before any operations of the servicing cycle may commence, or to shut off the metering pump and water valves if the vacuum supply ceases to function.

The sequence of operation of the servicing unit is as follows. First, an operator turns the servicing unit on. The air vent valve T (382) on the decontamination chamber is open. Vacuum valve V (364) is also opened and vacuum is applied to the decontamination chamber. Next, the operator places a canister 70 in the canister holding compartment 134. One of the position indicator switches 160 must be actuated, indicating that the canister is properly in position in the compartment. Next, the operator closes the door 164. This actuates a switch indicating that the door is locked. Next, the operator actuates the start cycle on the control panel. The canister compartment lift motor 170 is actuated, causing the canister to be raised and connected to the connector head 188. The valve R (376) on the conduit 200 is opened. Air vent T (382) on the decontamination chamber is closed, causing vacuum to be supplied to the suction tube 94 in the canister. Fluids withdrawn from the canister pass through conduit 200 into the decontamination chamber. When the canister 70 is empty, vacuum switch Q senses vacuum drop and sends a signal to the control unit to begin the washing cycle. The decontamination chamber continues to supply vacuum to the canister throughout the wash cycle, until the decontamination chamber is full.

For the canister washing cycle, three-way valve F is positioned to direct water flow to the canister. Valves V and C are opened, directing a cool water mixture to three-way valve F and to the canister inlet conduit 224. Valves B and C then close and valves A and D open. Valve H for concentrated detergent opens and the metering pump starts, drawing detergent from a reservoir. Detergent is directed by three-way valve N to the canister inlet conduit 224, with detergent mixing with the warm water flowing through the conduit 224. A hot rinse step follows, in which the metering pump stops, valves H, V and C are closed and valve A opens, so that hot water is directed to canister inlet conduit 224 by three-way valve F. There follows a warm water with disinfectant rinse; valves B and C close, valves A and D open, and valve K opens to allow the flow of disinfectant solution to the metering valve. There is then a final water rinse of the canister.

Once the canister washing cycle is completed, air vent T (382) on the decontamination chamber is opened. Valve R (376) is closed and the lift motor 170 is activated, lowering the canister receiving compartment 102, disconnecting the canister and lowering it to the rest position. The canister compartment door 136 is then unlocked. A graph of the operation of the servicing unit is further illustrated in the following Truth Table:

|  | S1 | S2 | S3 | S6 | S7 | S8 | S9 | S10 | S11 | S12 | S13 | S14 | S15 | S16 | S17 | S18 | S19 | S20 | S21 | S22 |
|---|---|---|---|---|---|---|---|---|---|---|---|---|---|---|---|---|---|---|---|---|
| TURN UNIT ON | C | C | O | O | O | O | O | O | O | O | O | O | C | O | O | O | O | O | O | O |
| PLACE CANISTER | C | C | C | O | O | O | O | O | O | O | O | O | C | O | O | O | O | O | O | O |
| CLOSE DOOR | C | C | C | C | O | O | O | O | O | O | O | O | C | O | O | O | O | O | O | O |
| LIFT BRACKET UP | C | C | C | C | O | C | O | O | O | O | O | O | C | O | O | O | O | O | O | O |
| START SEQUENCE | C | C | C | C | C | O | O | O | O | O | O | C | O | O | O | O | O | O | O | O |
| CANISTER EMPTY | C | C | C | C | C | O | O | C | O | C | O | C | O | O | O | O | O | O | O | O |
| RUN HOT | C | C | C | C | C | O | O | C | O | C | O | C | O | O | C | O | O | O | O | O |
| RUN WARM | C | C | C | C | C | O | O | C | O | C | O | C | O | O | C | C | O | O | O | O |
| RUN COOL | C | C | C | C | C | O | O | C | O | C | O | C | O | O | O | O | C | C | O | O |
| RUN COLD | C | C | C | C | C | O | O | C | O | C | O | C | O | O | O | O | O | C | O | O |
| RUN DISINFECTANT | C | C | C | C | C | O | O | C | O | C | O | C | O | O | C | C | O | O | O | C |
| RUN DETERGENT | C | C | C | C | C | O | O | O | O | C | O | C | O | O | C | C | O | O | C | O |
| CANISTER COMPLETE | C | C | C | C | C | O | C | O | C | C | O | O | C | O | O | O | O | O | O | O |
| DECONTAMINATION CHAMBER | C | C | C | C | C | O | O | O | C | O | O | O | C | C | O | O | O | O | O | O |
| HOT RINSE CYCLE | C | C | C | C | C | O | O | O | C | O | C | O | O | C | C | O | O | O | C | O |
| WARM RINSE | C | C | C | C | C | O | O | O | C | O | C | O | O | C | C | C | O | O | O | O |
| DISINFECT | C | C | C | C | C | O | O | O | C | O | C | O | O | O | O | O | O | C | O | C |
| DISINFECT COMPLETE | C | C | C | C | C | O | O | O | O | C | O | O | O | O | O | O | O | O | O | O |

C = SWITCH CLOSED, VALVE OPEN
O = SWITCH OPEN, VALVE CLOSED

The operation of the servicing unit has been described above with respect to the cleaning of a canister of the embodiment illustrated in FIGS. 1 and 2 of the drawings. The embodiment of the canister illustrated in FIG. 3 can also be readily cleaned using servicing unit 130 with minor modifications to the connector head 188. Since canister 1 shown in FIG. 3 has a sprayhead 57 built into its lid, a sprayhead in the connector head of the servicing unit is not required. Spray assembly 206 is therefore removed and replaced with a simple connector 202 and bracket (204) such that the connectors 202 are adapted to seal to both nipples 46 and 60 of canister 1.

The servicing unit described above can also be used for cleaning a canister of the embodiment illustrated in FIG. 10. The sprayhead may be modified, if necessary, with a projection in order to puncture the rupturable membrane 417 on port 416.

The preferred embodiment of the servicing unit includes a decontamination chamber 350, but in those cases where it is acceptable to put the body fluids from a canister directly into a sanitary sewer, without disinfecting them, the decontamination chamber may be omitted. A servicing unit without a decontamination chamber is described in my application Ser. No. 08/627,011, filed Apr. 3, 1996, the disclosure and drawings of which are hereby incorporated by reference.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A canister for receiving body fluids, comprising:
   (a) a body having side walls and a bottom;
   (b) a removable lid for sealably covering said body;
   (c) an inlet port in said lid for inflow of body fluids into said canister and for inflow of cleaning fluid into said canister;
   (d) an outlet port in said lid for suctioning said body fluids and said cleaning fluid from said canister;
   (e) a conduit in fluid communication with said outlet port and extending to the bottom of said canister;
   (f) a closure for closing said outlet port during said inflow of body fluids into said canister; and
   (g) a vacuum port in said lid for application of vacuum to said canister for inducing said inflow of body fluids into said canister.

2. A canister according to claim 1 further including a check valve on said lid operably coupled to said vacuum port for stopping said application of vacuum to said canister when said body fluids in said canister reach a predetermined level.

3. A canister according to claim 1 further comprising a body fluid inflow tube adapted for connection to said inlet port, comprising a tube having a section for attachment to a body fluid inlet tube and a section extending through said inlet port and into said canister.

4. A canister according to claim 1 wherein said conduit is removable from said lid.

5. A canister according to claim 1 wherein said outlet port is sealed by a puncturable membrane.

6. A canister according to claim 2 wherein said check valve comprises a floatball operably coupled to a needle valve.

7. A system for collecting and disposing of body fluids, comprising:
   (a) a canister for receiving said body fluids, comprising:
      (i) a body having side walls and a bottom;
      (ii) a removable lid for sealably covering said body;
      (iii) an inlet port in said lid for inflow of body fluids into said canister and for inflow of cleaning fluid into said canister;
      (iv) an outlet port in said lid for suctioning said body fluids and said cleaning fluid from said canister;
      (v) a conduit in fluid communication with said outlet port and extending to the bottom of said canister;
      (vi) a closure for closing said outlet port during said inflow of body fluids into said canister; and
      (vii) a vacuum port in said lid for application of vacuum to said canister for inducing said inflow of body fluids into said canister;

(b) a servicing unit for removing said body fluids from said canister and cleaning said canister, comprising:
  (i) an outlet conduit to conduct fluid from said canister;
  (ii) a supply of cleaning fluid capable of delivery into said canister;
  (iii) an inlet conduit for conducting said cleaning fluid from said supply to said canister;
  (iv) a connector for detachably connecting said outlet conduit to said outlet port in said lid and for detachably connecting said inlet conduit to said inlet port in said lid; and
  (v) a vacuum conduit operatively connecting a vacuum source to said outlet conduit for inducing a flow of fluid from said canister through said outlet conduit.

8. A system according to claim 7 further comprising:
  (a) a decontamination chamber in fluid communication with said outlet conduit, in which body fluid from said canister is brought into contact with a disinfecting fluid;
  (b) a first conduit to conduct fluid from said decontamination chamber to a drain;
  (c) a supply of disinfecting fluid capable of delivery into said decontamination chamber;
  (d) a second conduit for conducting said disinfecting fluid from said supply to said decontamination chamber; and
  (e) a vent for venting said decontamination chamber to atmosphere.

9. A system according to claim 7 further including a sprayhead in fluid communication with said inlet conduit and adapted to be inserted into said canister through said inlet port.

10. A system according to claim 7 wherein said system includes a detector in said servicing unit to detect whether a canister is correctly positioned in said servicing unit and wherein said lid of said canister comprises a portion adapted to actuate said detector when said canister is correctly positioned.

11. A system according to claim 7 further including a canister lifter for raising and lowering said canister between a first, lower position and a second, upper, position in which said outlet port of said canister is operatively connected to said outlet conduit and said inlet port of said canister is operatively connected to said inlet conduit.

12. A system according to claim 11 wherein said canister lifter comprises a canister compartment to hold said canister and a vertical lift mechanism to raise and lower said compartment.

13. A system according to claim 12 wherein said canister compartment can move to a plurality of operative positions to connect canisters of different heights to said inlet and outlet conduits of said servicing unit.

14. A servicing unit for cleaning a canister of body fluids and disposing of said fluids, said canister having a lid with an outlet port and an inlet port, comprising:
  (a) an outlet conduit to conduct fluids from said canister;
  (b) an inlet conduit to conduct cleaning fluid from a source of said cleaning fluid to said canister;
  (c) a connector for detachably connecting said outlet conduit to said outlet port in said lid of said canister and for detachably connecting said inlet conduit to said inlet port in said lid of said canister;
  (d) a vacuum conduit operatively connecting a vacuum source to said outlet conduit for inducing a flow of fluid from said canister through said outlet conduit.

15. A canister for receiving body fluids, comprising:
  (a) a body having side walls and a bottom;
  (b) a removable lid for sealably covering said body;
  (c) an inlet port in said lid for inflow of body fluids into said canister;
  (d) an outlet port in said lid for suctioning said body fluids from said canister;
  (e) a conduit in fluid communication with said outlet port and extending to the bottom of said canister;
  (f) a closure for closing said outlet port during said inflow of body fluids into said canister; and
  (g) a vacuum port in said lid for application of vacuum to said canister for inducing said inflow of body fluids into said canister.

16. A system according to claim 7 wherein said canister further comprises a check valve on said lid operably coupled to said vacuum port for stopping said application of vacuum to said canister when said body fluids in said canister reach a pre-determined level.

17. A lid for covering a canister body, said lid and canister body together forming a canister for receiving fluids, said canister body having side walls and a bottom, said lid comprising:
  (b) an inlet port in said lid for inflow of fluids into said canister;
  (b) an outlet port in said lid for outflow of fluids from said canister;
  (c) a conduit in fluid communication with said outlet port, said conduit extending to said bottom of said canister body when said lid is placed in covering relation to said canister body;
  (d) a vacuum port in said lid for application of vacuum to said canister for inducing said inflow of fluids into said canister; and
  (e) a check valve on said lid operably coupled to said vacuum port for stopping said application of vacuum to said canister when said fluids in said canister reach a pre-determined level.

* * * * *